United States Patent
Grooters et al.

(10) Patent No.: US 6,254,578 B1
(45) Date of Patent: Jul. 3, 2001

(54) AORTIC CANNULA WITH TAPERED TIP

(76) Inventors: Ronald K. Grooters, 5535 Glen Oaks Pt., West Des Moines, IA (US) 50266-6627; Robert J. Todd, 3415 S. Eastwood Dr., Salt Lake City, UT (US) 84109

( * ) Notice: Subject to any disclaimer, the term of this patent is extended or adjusted under 35 U.S.C. 154(b) by 0 days.

(21) Appl. No.: 09/221,903

(22) Filed: Dec. 28, 1998

Related U.S. Application Data

(63) Continuation-in-part of application No. 08/940,745, filed on Sep. 30, 1997, now Pat. No. 5,876,383.

(51) Int. Cl.⁷ .................................................... A61M 5/00
(52) U.S. Cl. ............................................................ 604/264
(58) Field of Search .................................. 604/264, 272, 604/523, 239, 500, 506, 532

(56) References Cited

U.S. PATENT DOCUMENTS

| | | |
|---|---|---|
| 191,879 | 6/1877 | Pfarre . |
| 1,998,225 | 4/1935 | Dow . |
| 3,828,767 | 8/1974 | Spiroff . |
| 4,198,984 | 4/1980 | Taylor ................................. 128/349 |
| 4,276,880 | 7/1981 | Malmin ............................... 128/221 |
| 4,361,152 | 11/1982 | Patel ...................................... 604/99 |
| 4,368,738 | 1/1983 | Tersteegen et al. . |
| 4,617,019 | 10/1986 | Fecht et al. . |
| 4,643,712 | 2/1987 | Kulik et al. ............................... 604/4 |
| 4,795,446 | 1/1989 | Fecht ................................... 604/264 |
| 4,863,441 | 9/1989 | Lindsay et al. ..................... 604/280 |
| 5,044,369 | 9/1991 | Sahota . |
| 5,084,033 | 1/1992 | O'Neill et al. . |
| 5,147,334 | 9/1992 | Moss .................................... 604/264 |
| 5,167,645 | 12/1992 | Castillo . |
| 5,259,371 | 11/1993 | Tonrey ............................. 128/200.26 |
| 5,290,267 | 3/1994 | Zimmermann . |
| 5,320,599 | 6/1994 | Griep et al. ............................. 604/35 |
| 5,344,412 | 9/1994 | Wendell et al. ..................... 604/280 |
| 5,354,288 | 10/1994 | Cosgrove et al. .................... 604/264 |
| 5,360,414 | 11/1994 | Yarger ................................. 604/264 |
| 5,364,373 | 11/1994 | Waskonig et al. . |
| 5,389,074 | 2/1995 | Parker et al. . |
| 5,407,441 | 4/1995 | Greenbaum ......................... 604/280 |
| 5,451,216 | 9/1995 | Quinn .................................. 604/270 |
| 5,456,675 | 10/1995 | Wolbring et al. . |
| 5,480,392 | 1/1996 | Mous . |
| 5,599,322 | 2/1997 | Quinn . |
| 5,616,137 | 4/1997 | Lindsay ............................... 604/264 |
| 5,643,226 | 7/1997 | Cosgrve et al. . |
| 5,685,865 | 11/1997 | Cosgrove et al. . |
| 5,749,889 | 5/1998 | Bacich et al. . |
| 5,792,099 | * 8/1998 | DeCamp et al. ................. 604/239 X |

FOREIGN PATENT DOCUMENTS

| | | |
|---|---|---|
| 0092927 B1 | 8/1986 | (EP) . |
| 0159773 B1 | 6/1988 | (EP) . |
| 0705617 A1 | 4/1994 | (EP) . |
| 0612536 A1 | 8/1994 | (EP) . |
| WO 96/18428 | 6/1996 | (WO) . |

* cited by examiner

*Primary Examiner*—Manuel Mendez
(74) *Attorney, Agent, or Firm*—Zarley, McKee, Thomte, Voorhees & Seas

(57) ABSTRACT

An improved aortic cannula is provided for use in heart by-pass surgery. The cannula includes an elongated tube with a terminal end. The terminal end has a ramped surface leading to the discharge opening. The ramped surface terminates in a lip having a tapered leading edge with a point for insertion of the cannula into the aorta. The tapered leading edge spreads a previously made incision to facilitate entry of the terminal end of the cannula into the aorta. With the improved cannula of the present invention, the size of the incision in the aorta is minimized and the damage or tearing of the aorta is eliminated or minimized. This ease of insertion also reduces the time required in the procedure of inserting the cannula into the aorta.

14 Claims, 2 Drawing Sheets

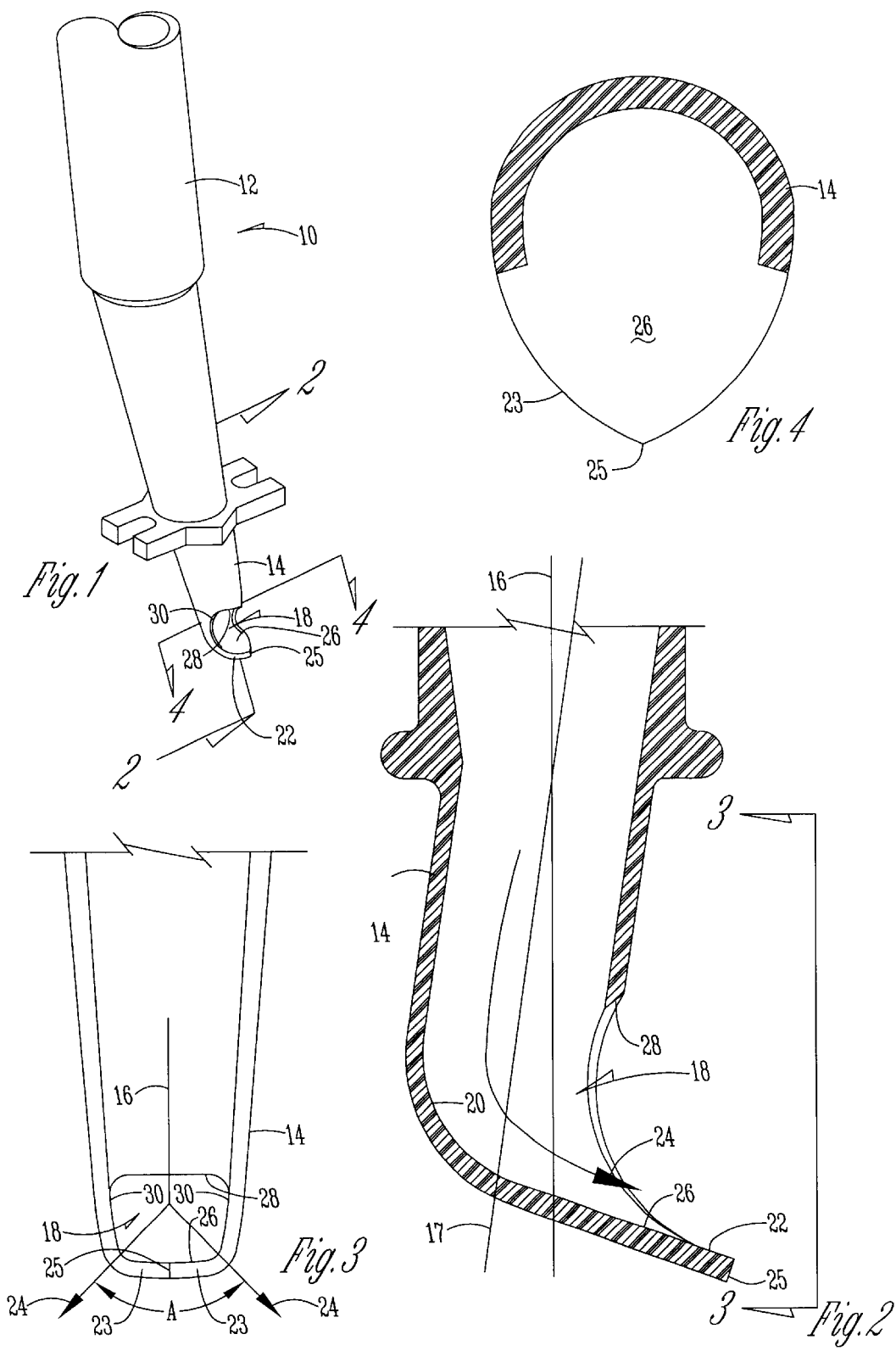

AORTIC CANNULA WITH TAPERED TIP

RELATED APPLICATION

This application is a continuation-in-part of applications Ser. No. 08/940,745 filed Sep. 30, 1997, now U.S. Pat. No. 5,876,383.

BACKGROUND OF THE INVENTION

The present invention relates generally to medical devices and, in particular, aortic cannulas. Aortic cannulas are used to return blood to the aorta while the heart is by-passed during heart surgery. These cannulas are purposely made with small diameters to minimize disruption to the aorta, which in many heart surgery patients have advanced complex atherosclerotic plaque with adherent blood from bithrombi.

Aortic cannulas generally comprise an elongated tube having a terminal end. This terminal end is inserted through an incision in the aorta. The terminal end of a conventional cannula is blunt and will encounter resistance from the aorta when inserted through the incision made by the surgeon. Such resistance may lead to damage to the aorta or tearing along the incision line. It is advantageous for patient recovery to minimize any damage to the aorta and the size of the incision in the aorta. Moreover ease of insertion of the cannula may lead to reduced time of operation, additionally assisting in patient well-being.

Therefore, a primary objective of the present invention is the provision of an improved aortic cannula which facilitates the ease of insertion of the terminal end into the aorta.

Another objective of the present invention is a provision of an improved aortic cannula which requires a minimal incision size in the aorta.

A further objective of the present invention is the provision of an improved aortic cannula which minimizes injury or damage to the aortic tissues.

These and other objectives will become apparent from the following description of the invention.

SUMMARY OF THE INVENTION

The improved aortic cannula of the present invention includes an elongated tube having a terminal end. The tube has an internal curved surface leading to an enlarged opening adjacent the terminal end of the cannula. The curved surface terminates in a lip extending beyond the perimeter of the tubular cannula. The lip has a laterally tapered leading edge with a pointed tip to provide quick and easy insertion through an incision in the aorta. This tapered lip is inserted in a manner which minimizes the needed incision size and reduces damage to the aorta. Moreover, the tapered lip also reduces the time necessary for insertion of the cannula into the aorta.

BRIEF DESCRIPTION OF THE DRAWINGS

FIG. 1 is a perspective view of the improved aortic cannula of the present invention.

FIG. 2 is a sectional view of the terminal end of the aortic cannula shown along lines 2—2 of FIG. 1.

FIG. 3 is an elevation view of the aortic cannula taken along lines 3—3 of FIG. 2.

FIG. 4 is a sectional view taken along lines 4—4 of FIG. 1 showing the laterally tapered lip of the cannula.

DETAILED DESCRIPTION OF THE PREFERRED EMBODIMENT

Figure 5:
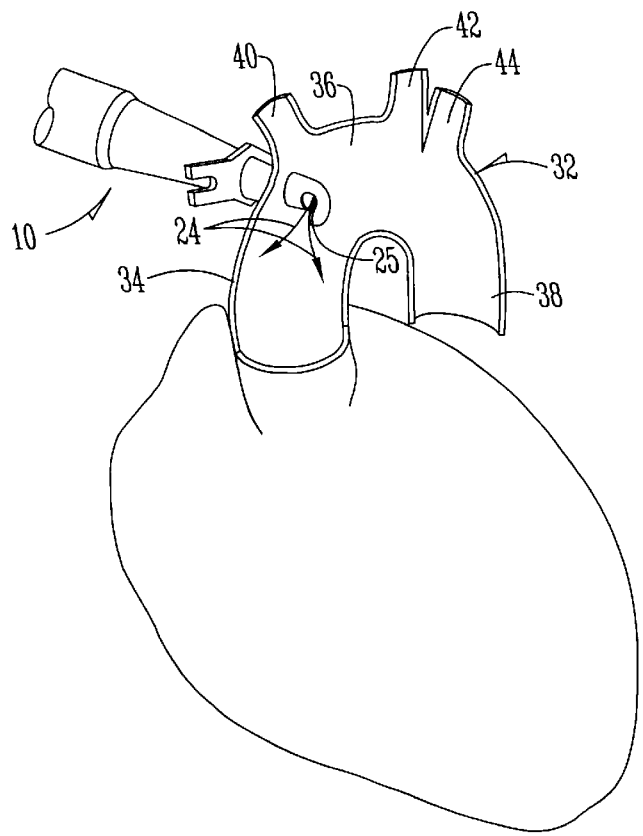
FIG. 5 is a schematic diagram of the heart and its primary blood vessels with the aortic cannula of the present invention inserted into the ascending aorta.

The present invention will be described as it applies to its preferred embodiment. It is not intended that the present invention be limited to the described embodiment. It is intended that the invention cover all alternatives, modifications, and equivalencies which may be included within the spirit and scope of the invention.

The improved aortic cannula of the present invention is generally designated by the reference numeral 10 in the drawings. The cannula 10 comprises an elongated tube 12 with a terminal end 14. As best seen in FIG. 2, the terminal end 14 is angled or tilted slightly with respect to the longitudinal axis 16 of the tube 12. Preferably, by way of example and not limitation, the relative angle between the axis 17 of the terminal end 14 and the longitudinal axis 16 of the tube 12 is approximately 8° to 18°. The diameter of the tube 12 may taper toward the terminal end 14.

An enlarged opening 18 is provided in the terminal end 14. A curved or ramped surface 20 directs blood along a lip 22 extending from the terminal end 14 at approximately 70°–90° relative to the longitudinal axis 16 of the tube 12. The lip 22 extends beyond the perimeter of the tube 12, as best seen in FIG. 2. The opening 18, ramped surface 20 and lip 22 allow the blood to be forced through the cannula 10 at a lower pressure. The large opening also reduces the velocity of the exiting blood. The ramped surface 20 and the lip 22 direct the blood toward the ascending aorta, as indicated by arrow 24, at an angle substantially 70°–90° from the longitudinal axis 16 of the tube 12. Without the extended lip 22, which in effect extends the lower edge 26 of the opening 18 beyond the top edge 28 of the opening, the ramped surface 20 alone will only direct the exiting blood at an angle approximately 45° from the longitudinal axis 16 of the tube 12. The width of the opening 18 also controls the width of the broadcast of the exiting blood. The opening 18 extends approximately 180° from one side 30 to the other side 30, thereby allowing a broadcast of exiting blood with a radius of approximately 900, as indicated by angle A in FIG. 3. The large size of the opening 18 also decreases the velocity of the blood exiting from the cannula 10.

The leading edge 23 of the lip 22 is tapered from side to side, so as to come to a point 25, as best seen in FIG. 4. This laterally tapered edge 23 allows for quick and easy insertion on the cannula 10 into the aorta, as described below. The point 25 is not sharp, and is not designed to pierce the aorta. Rather, the point 25 facilitates insertion of the lip 22 and terminal end 16 of the cannula 10 through a surgical incision in the aorta, as described below.

In FIG. 5, the aorta is designated by the reference numeral 32. The aorta 32 includes three main sections, the ascending aorta 34, the transverse aortic arch 36, and the descending aorta 38. The aortic arch 36 is the primary area where atherosclerotic plaque 46 is found in patients needing heart bypass surgery. Branching from the aorta 32 are three large arteries, the innominate artery 40, the left carotid 42, and the left subclavian 44.

Figure 6:
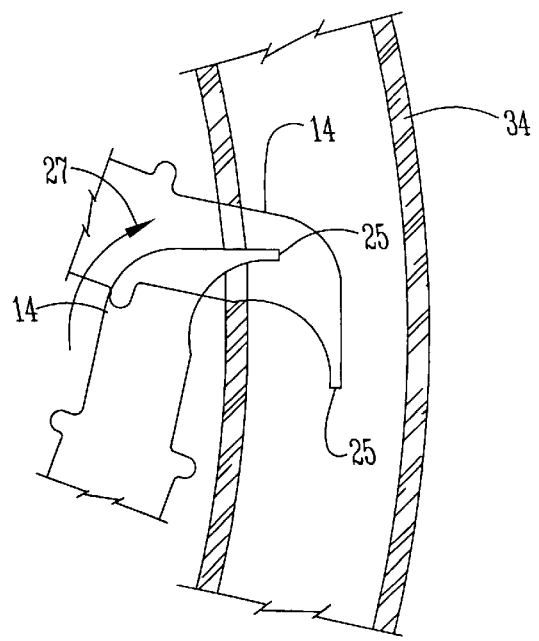
FIG. 6 is a schematic sectional view showing the initial and complete insertion positions of the cannula in the aorta.

After an incision is made by the surgeon in the ascending aorta 34, the cannula 10 is positioned such that the tube 12 is relatively close to the aorta. The pointed tip 25 is inserted into the incision and the cannula 10 is rotated upwardly as indicated by the arrow 27 in FIG. 6, such that the tube 12 extends away from the aorta 32. The pointed tip 25 and tapered edge 23 function to spread and open the incision for quick and easy insertion of the cannula terminal end 14, as seen in FIG. 5. In FIG. 6, the initial insertion position of the point 25 and lip 22 is shown in broken lines, while the final insertion position of the terminal end 14 is shown in solid lines. This process is reversed for removal of the cannula 10 from the aorta 32.

In the present invention, the blood flow from the cannula 10 is preferably directed toward the ascending aorta, and away from the aortic arch and atherosclerotic plaque. Even if the blood flow is directed at the aortic arch, the low pressure, low velocity, broad band flow minimizes the risk of dislodging plaque from the artery wall.

Thus, the aortic cannula 10 of the present invention is quickly and easily inserted through a minimally sized incision in the aorta 32, thereby reducing risk of damage to the aortic wall and optimizing patient recovery. Furthermore, by directing blood flow away from the aortic arch 36, the improved cannula 10 reduces the chance that the plaque 46 will become dislodged during cardiac bypass surgery, and thus, helps to reduce the risk of embolism and strokes. In comparison, with prior art cannulas, the blood directed towards the aortic arch 36 may dislodge plaque 46, which then can enter the blood stream and cause a stroke.

Whereas the invention has been shown and described in connection with the preferred embodiments thereof, it will be understood that many modifications, substitutions, and additions may be made which are within the intended broad scope of the following claims. From the foregoing, it can be seen that the present invention accomplishes at least all of the stated objectives.

What is claimed is:

1. An aortic cannula comprising:
   an elongated tube having a longitudinal axis and a terminal end with an opening therein;
   a lip extending from the terminal end adjacent the opening and having a tapered leading edge to facilitate insertion of the terminal end into an incision in the aorta.
2. The cannula of claim 1 wherein the lip terminates in a point.
3. The cannula of claim 1 wherein the lip extends beyond the perimeter of the tube.
4. The cannula of claim 3 wherein the lip extends approximately 70°–90° relative to the longitudinal axis.
5. The cannula of claim 1 wherein the opening is disposed on the tube to direct blood toward the ascending aorta.
6. The cannula of claim 1 wherein the opening has a substantial width permitting a fanned broadcast of blood from the opening.
7. The cannula of claim 6 wherein the fanned broadcast of blood has a radius of approximately 90°.
8. The cannula of claim 1 wherein the terminal end of the tube is angled with respect to the longitudinal axis.
9. A method of inserting a cannula into the aorta, the cannula having a terminal end with an opening and a lip with a tapered leading edge extending from the terminal end adjacent the opening, the method comprising:
   making an incision in the aorta;
   inserting the lip of the cannula through the incision;
   rotating the cannula away from the aorta such that the lip spreads the incision; and
   pushing the terminal end of the cannula through the spread incision.
10. The method of claim 9 further comprising orienting the opening so as to be directed away from the aortic arch.
11. An aortic cannula comprising:
    an elongated tube having a longitudinal axis and a terminal end with a side opening therein;
    a lip extending from the terminal end adjacent the opening, the lip extending laterally beyond the perimeter of the tube and having a tapered leading edge to facilitate insertion of the terminal end into an incision in the aorta.
12. The cannula of claim 11 wherein the lip terminates in a point.
13. The cannula of claim 11 wherein the lip extends approximately 70 degrees to 90 degrees relative to the longitudinal axis.
14. The cannula of claim 11 wherein the side opening has an upper edge that is radially flush with the perimeter of the tube.

* * * * *